United States Patent [19]

Jensen

[11] Patent Number: 4,813,874
[45] Date of Patent: Mar. 21, 1989

[54] ETCHED PORCELAIN VENEER CROWNS

[75] Inventor: Mark E. Jensen, Iowa City, Iowa

[73] Assignee: Terec USA, Sioux City, Iowa

[21] Appl. No.: 23,594

[22] Filed: Mar. 9, 1987

[51] Int. Cl.$^4$ ............................................... A61C 5/08
[52] U.S. Cl. .................................. 433/219; 433/212.1
[58] Field of Search ............. 433/212, 218, 219, 228.1

[56] References Cited

U.S. PATENT DOCUMENTS

| | | | |
|---|---|---|---|
| 4,117,595 | 10/1978 | Ibsen et al. | 433/218 |
| 4,376,673 | 3/1983 | Cheung | 433/218 X |
| 4,514,527 | 4/1985 | Bowen | 433/288.1 X |
| 4,593,054 | 6/1986 | Asmussen et al. | 433/228.1 X |
| 4,604,059 | 8/1986 | Klaus et al. | 433/218 X |

Primary Examiner—Samuel Scott
Assistant Examiner—Carl D. Price
Attorney, Agent, or Firm—Henderson & Sturm

[57] ABSTRACT

A method for preparing and fitting a partial or full veneer etched porcelain crown on a tooth preparation. The method includes the steps of preparing a veneer porcelain crown; etching the interior surface of the porcelain crown and the remaining tooth enamel of the tooth preparation; applying a silane-coupling agent to the etched surface of the porcelain crown; applying a layer of dentin bonding agent to the exposed dentin of the tooth preparation; applying a layer of unfilled resin to the silane-coupled etched porcelain surface and to the etched enamel and dentin bonding agent on the tooth preparation; applying a layer of bonding resin to overlay the unfilled resin on the tooth preparation; positioning the veneer crown on the tooth preparation; and curing the bonding resin. The laminate structure thus formed has a natural appearance and is highly fracture resistant.

3 Claims, 1 Drawing Sheet

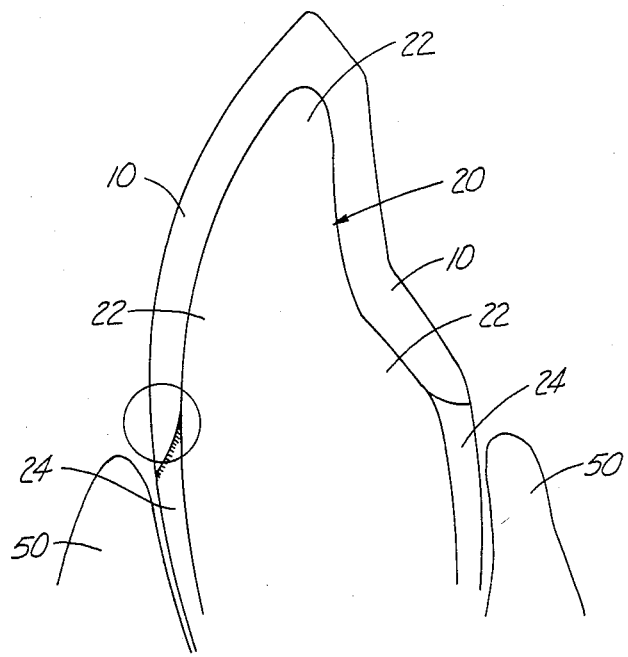
Fig. 1
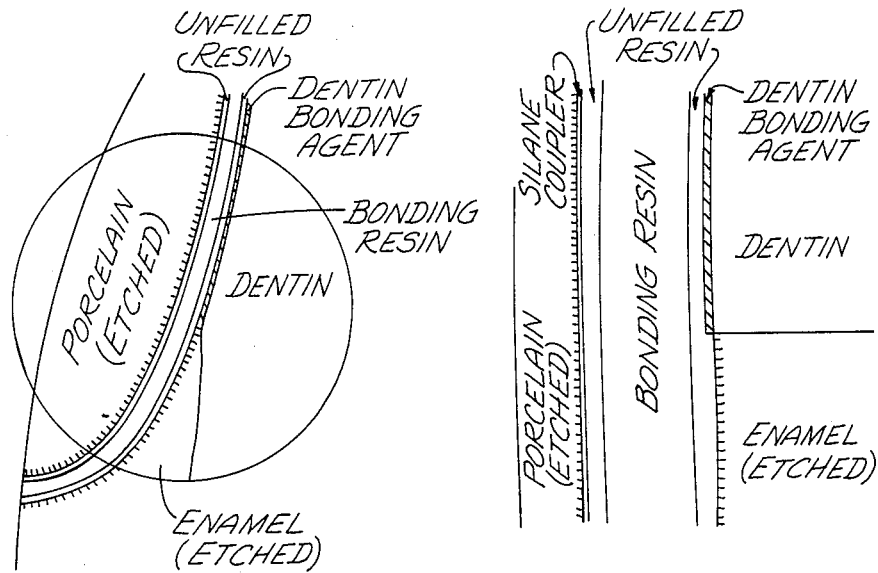
Fig. 2
Fig. 3

ETCHED PORCELAIN VENEER CROWNS

TECHNICAL FIELD

This invention relates to dental restorations and more particularly to porcelain partial or full veneer crowns.

BACKGROUND ART

Crown restorations using metals and porcelain are well known. Crowns fabricated from metals have high fracture resistance and are conventionally used in situations where natural appearance is not the primary concern. Porcelain crowns have the advantage of natural appearance; however, presently available porcelain crowns have low fracture resistance.

Those concerned with these and other problems recognize the need for an improved porcelain crown.

DISCLOSURE OF THE INVENTION

The present invention provides a method of preparing and fitting a partial or full veneer etched porcelain crown on a tooth preparation. The method includes the steps of preparing a veneer porcelain crown; etching the interior surface of the porcelain crown and the remaining tooth enamel of the tooth preparation; applying a silane-coupling agent to the etched surface of the porcelain crown; applying a layer of dentin bonding agent to the exposed dentin of the tooth preparation; applying a layer of unfilled resin to the silane-coupled etched porcelain surface and to the etched enamel and dentin bonding agent on the tooth preparation; applying a layer of bonding resin to overlay the unfilled resin on the tooth preparation; positioning the veneer crown on the tooth preparation; and curing the bonding resin. The laminate structure thus formed has a natural appearance and is highly fracture resistant.

An object of the present invention is the provision of an improved porcelain crown dental restoration.

Another object is to provide a porcelain crown having high fracture resistance.

A further object of the invention is the provision of a porcelain crown dental restoration that is easily fitted.

Still another object is to provide a porcelain crown that is durable and inexpensive.

A still further object of the present invention is the provision of a porcelain crown dental restoration that has a natural appearance.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a schematic cross sectional view of a tooth restoration using the etched porcelain crown of the present invention;

FIG. 2 is an enlarged schematic view of the isolated area of FIG. 1 showing the position of the porcelain with respect to the remaining enamel and dentin of a prepared tooth; and FIG. 3 is a greatly enlarged schematic view showing the laminate including the porcelain veneer crown, the bonding agents, and enamel and dentin of the prepared tooth.

BEST MODE FOR CARRYING OUT THE INVENTION

Referring now to the drawings, wherein like reference numerals designate identical or corresponding parts throughout the several views, FIG. 1 shows a tooth restoration comprising a porcelain veneer crown (10) bonded to a prepared tooth (20). The walls of the crown (10) are generally about 0.5 mm thick and extend down to the vicinity of the gum (50). The prepared tooth (20) includes exposed dentin (22) and typically also includes remaining areas of enamel (24).

The following examples are illustrative of the best mode for carrying out the invention. They are obviously not to be construed as limitative of the invention since various other embodiments can readily be evolved in view of the teachings provided herein.

EXAMPLE 1

"Etched Porcelain Crown Preparation"

A tooth color shade is first selected using a Lumin shade guide and CU-5 photographs are taken.

Local anesthesia is obtained in normal manner selected for the patient.

The tooth is prepared by removing old restorations, caries and grossly undermined tooth structure. A small amount of calcium-hydroxide sub-base is used if the prepared surface is less than 0.5 mm from the pulp. Conditioner is used on the dentin for twenty seconds and rinsed well with an air-water spray. Glass-ionomer base can be used if the preparation is undermined and the impression may be distorted. The base may also be placed by using the dentin bonding kit (GLUMA/LUMIFOR). The name GLUMA is the trademark of Boyer AG for dentin bonding. The preparation must have definite margins that can be isolated for the crown to be properly seated. If definite margins cannot be isolated, electro-surgery is performed.

The finish lines or margins of the preparation are then checked and the provisional restoration is fabricated. This is done using putty or an alginate impression and temporary material of choice.

The internal form of preparation is checked and any necessary changes are made. A retraction cord is placed if it is required and an impression is taken with polyvinyl-siloxane or poly-ether material. An inspection is then made for highly visible margins.

Centric relationship records are taken with any dental material and the provisional restoration is cemented with non-eugenol material such as Freegenol or polycarboxylate cement.

An alginate impression of the opposing arch is then taken.

A partial or full veneer porcelain crown (10) is then fabricated and the internal surface of the crown (10) is etched with a suitable material such as etching gel. (37% ortho-phosphoric acid).

EXAMPLE 2

"Crown Seating"

The area for crown seating is anesthetized and the provisional restorations are removed. The tooth preparation is then cleaned with a prophy-cup and pumice.

The etched porcelain crown (10) is carefully positioned over the tooth preparation and checked for proximal contacts and margins.

When the crown (10) is seating completely, it is rinsed well and dried with acetone. A silane-coupler (Scotchprime) is applied to the etched surface of the porcelain crown (10) and allowed to dry.

Etching gel (37% ortho-phosphoric acid) is then placed on any remaining enamel on the tooth preparation. After a 15 second waiting period, the enamel is rinsed well and dried with an air syringe.

The dentin surface of the tooth preparation is treated with GLUMA cleanser (an aqueous solution of Ethylene-diamine tetra acetic acid (EDTA)) for 60 seconds, rinsed and then dried. GLUMA dentin bond (an aqueous solution of hydroxyethylmethacrylate (HEMA) containing slutaraldehydes for bonding with subsequent Bis-GMA resin) is then placed and let stand 60 seconds. It may be blown to a thin layer if necessary but not rinsed. Unfilled resin (Scotchbond) (trademark of 3M Company which is a chlorinated phosphorus esther of Bis-GMA - (Bis glycodylemeth-acrylate)) is then placed in the crown (10) and on the treated tooth preparation. The unfilled resin is only used as a wetting agent and therefore must be blown to a thin layer.

Any necessary tint is placed in the crown (10) together with a thin layer of bonding resin (Chameleon a product of Myron's International and Pentron Corporation or a Dual cure material Vradent's Dual cement—which are low viscosity filled-resin—66% filled with radiopaque glass—BisGMA resin with filler having mean particle size of about 2 microns). If a light-curing resin is used, the operating light must be turned down. The crown (10) may be retinted, if necessary, by removing and cleaning with acetone.

The crown (10) is held in place and cured with a photo-unit for twenty seconds from the buccal surface and twenty seconds from the lingual surface. Excess resin must be removed with cotton and floss before the photo-cure.

The occlusion must be very carefully checked with paper and shimstock to eliminate any interferences and obtain ideal contacts. Occlusion cannot be safely checked before the resin has been photo-cured.

The restoration is finally polished or adjusted with diamonds and water-spray and finished with a 10 or 15 micron particle size finishing diamond before using discs. Soflex discs with lubricant can then be used followed by a prophy cup with "diamond" paste.

Pre and post operative photographs are taken to complete the treatment record. Anterior teeth need a labial 1:1 shot and posteriors need both.

FIGS. 2 and 3 illustrate the construction of the laminate formed by the method of preparing and fitting a partial or full veneer crown (10) on a a tooth preparation. It is to be understood that the surface of the tooth preparation could be comprised of dentin only, as well as the dentin-enamel combination illustrated.

Thus, it can be seen that at least all of the stated objectives have been achieved.

Obviously, many modifications and variations of the present invention are possible in light of the above teachings. It is therefore to be understood that, within the scope of the appended claims, the invention may be practised otherwise than as specifically described.

I claim:

1. A method of fitting a veneer porcelain crown on a tooth preparation having exposed areas of dentin, comprising the steps of:
   forming a veneer porcelain crown to conform to the surface of a tooth preparation;
   etching the interior surface of said crown and silane-coupling said etched surface;
   applying a layer of dentin bonding agent to the exposed areas of dentin on the surface of the tooth preparation;
   applying a layer of unfilled resin to each of the silane-coupled surface of the crown and the layer of dentin bonding agent;
   applying a layer of bonding resin over the layer of unfilled resin on the tooth preparation; and,
   positioning the crown on the tooth preparation and curing the bonding resin to form a laminate structure resistant to fracture.

2. A method of fitting a veneer porcelain crown on a tooth preparation having both exposed areas of dentin and remaining areas of tooth enamel, comprising the steps of:
   forming a veneer porcelain crown to conform to the surface of a tooth preparation;
   etching the interior surface of said crown and silane-coupling said etched surface;
   applying a layer of dentin bonding agent to exposed dentin on the surface of the tooth preparation;
   etching remaining areas of tooth enamel on the surface of the tooth preparation ;
   applying a layer of unfilled resin to each of the silane-coupled surface of the crown, the layer of dentin bonding agent, and the etched enamel;
   applying a layer of bonding resin over the layer of unfilled resin on the tooth preparation; and,
   positioning the crown on the tooth preparation and curing the bonding resin to form a laminate structure resistant to fracture.

3. The method as in claims 1 and 2 wherein the dentin bonding agent comprises:
   hydroxyethylmethacrylate.

* * * * *